United States Patent [19]
Nizzola

[11] Patent Number: 5,356,409
[45] Date of Patent: Oct. 18, 1994

[54] EQUIPMENT FOR THE CORRECTION OF ASTYGMATISM BY REMODELLING THE CORNEAL SURFACE BY MEANS OF PHOTO-ABLATION

[75] Inventor: Guido M. Nizzola, Modena, Italy

[73] Assignee: Nibatec S.A., Chiasso, Switzerland

[21] Appl. No.: 977,579

[22] Filed: Nov. 17, 1992

[30] Foreign Application Priority Data

Nov. 21, 1991 [IT] Italy ................ MO91A000167

[51] Int. Cl.⁵ .................................... A61B 17/32
[52] U.S. Cl. ................................ 606/5; 606/4
[58] Field of Search .................... 606/4, 5, 6, 3

[56] References Cited

U.S. PATENT DOCUMENTS 4,732,148  3/1988  L'Esperance, Jr. .............. 606/5
5,152,759 10/1992  Parel et al. ...................... 606/5

FOREIGN PATENT DOCUMENTS 9111158  8/1991  World Int. Prop. O. ......... 606/5

Primary Examiner—Peter A. Aschenbrenner
Assistant Examiner—Sonya C. Harris
Attorney, Agent, or Firm—Darby & Darby

[57] ABSTRACT

The invention relates to equipment for the correction of astygmatism by modelling of the corneal surface by means of photo-ablation. A laser beam produced by an excimer laser is used, which is masked by a special mask (1) in such a way that, at each application, a pre-established surface of the cornea (3) is struck, from which cornea (3) a very thin uniform layer of tissue is removed.

12 Claims, 5 Drawing Sheets

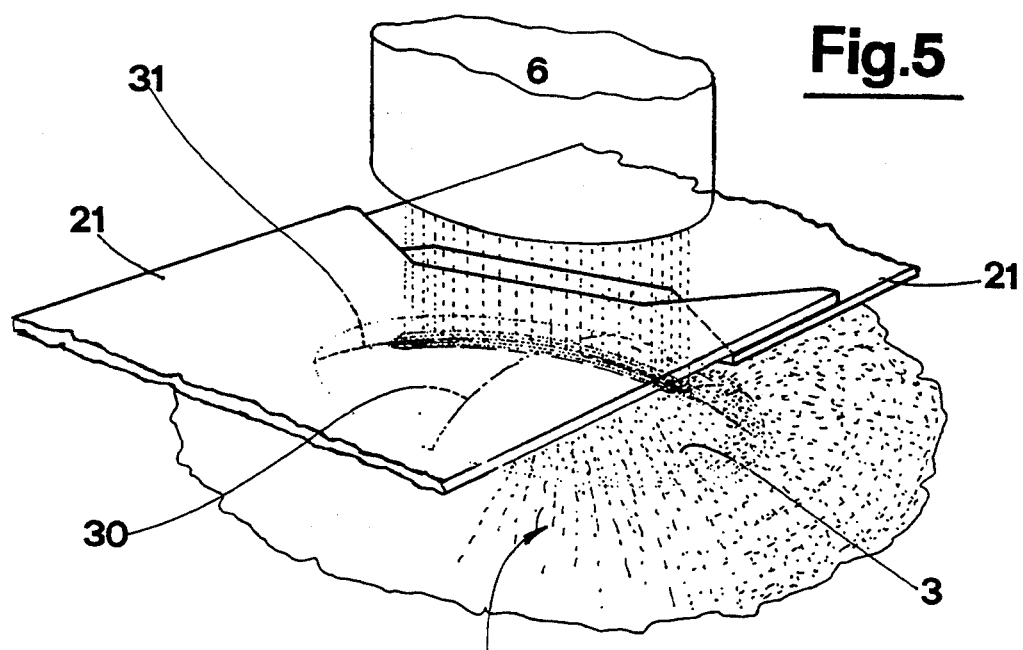
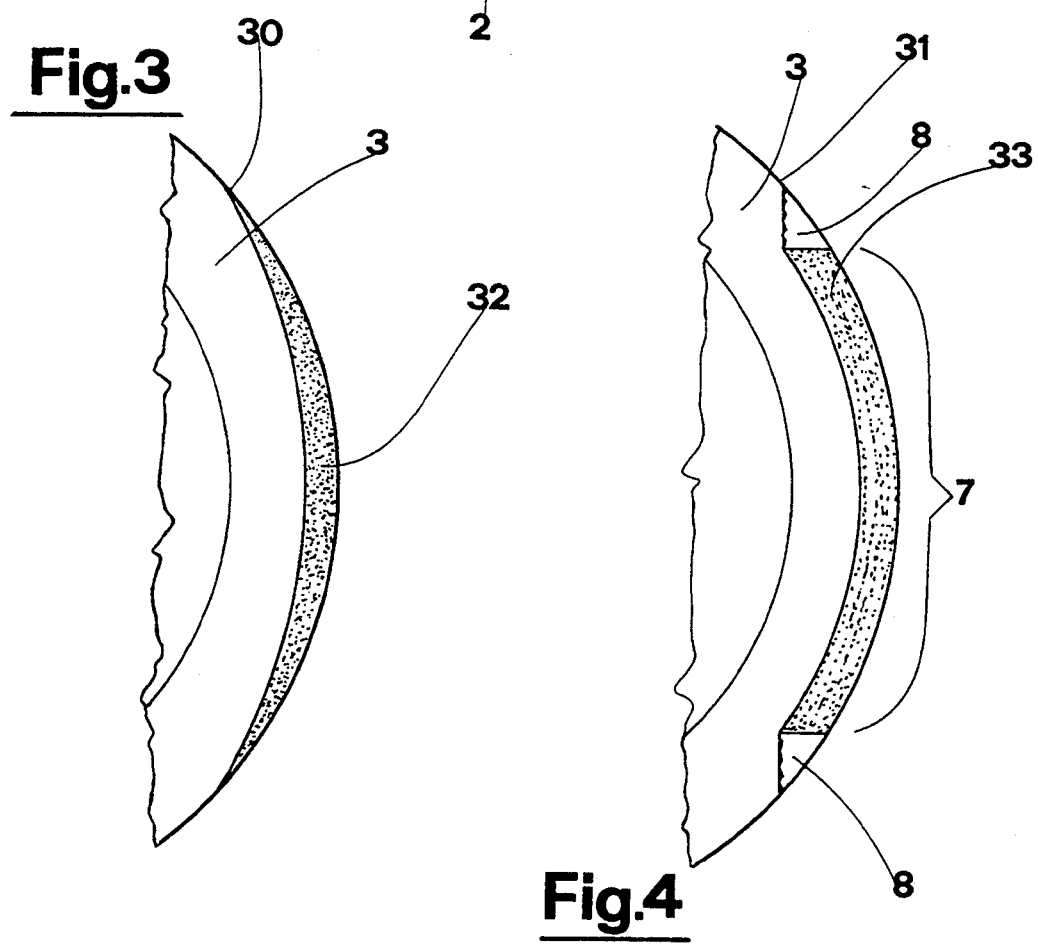

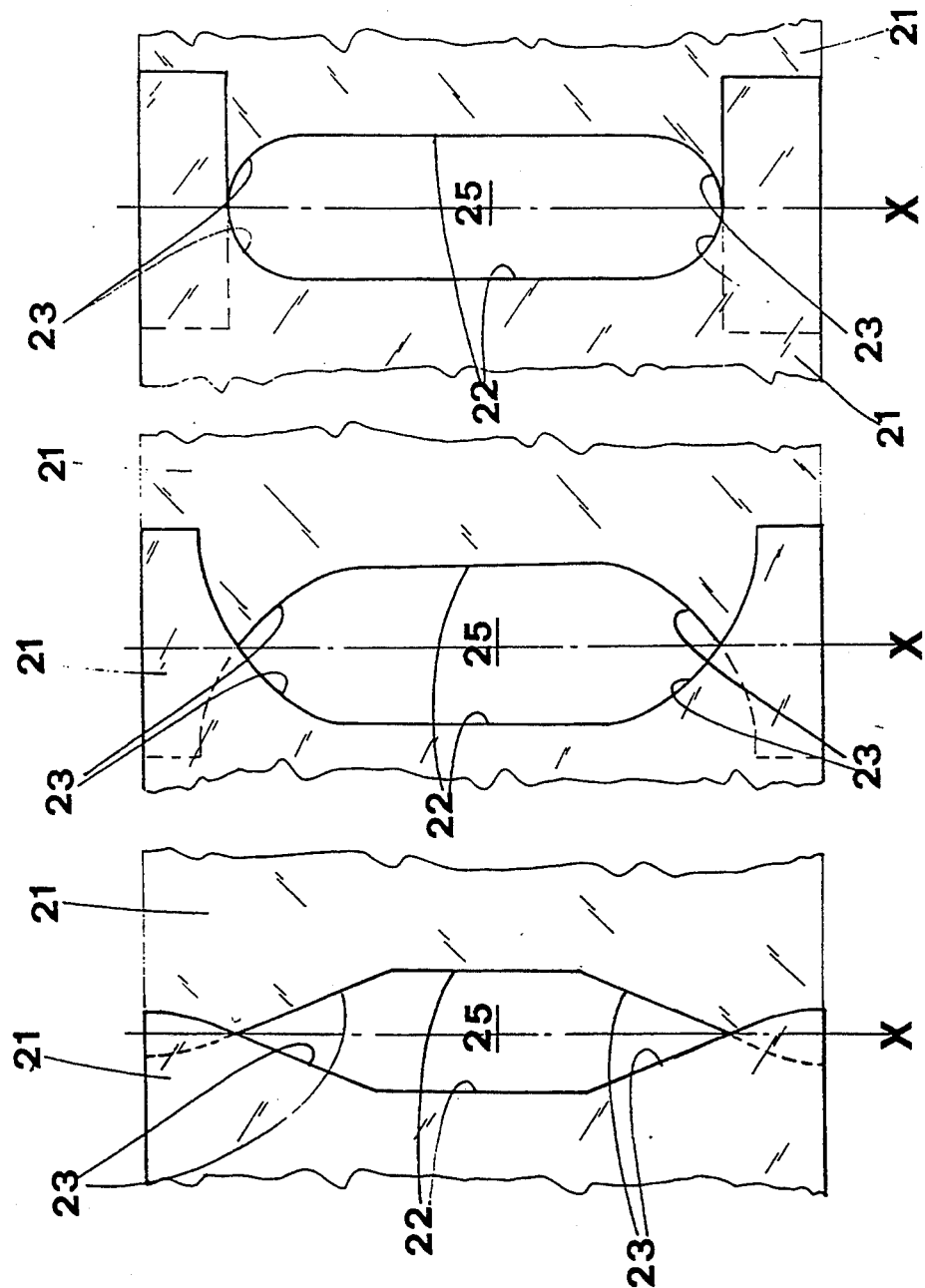

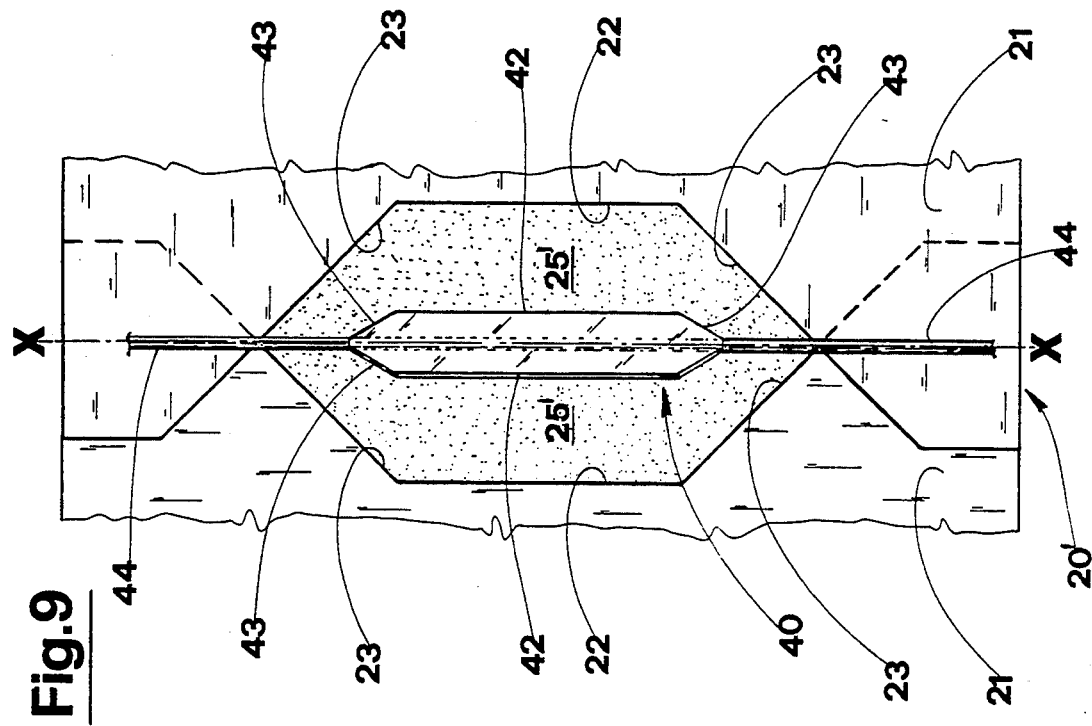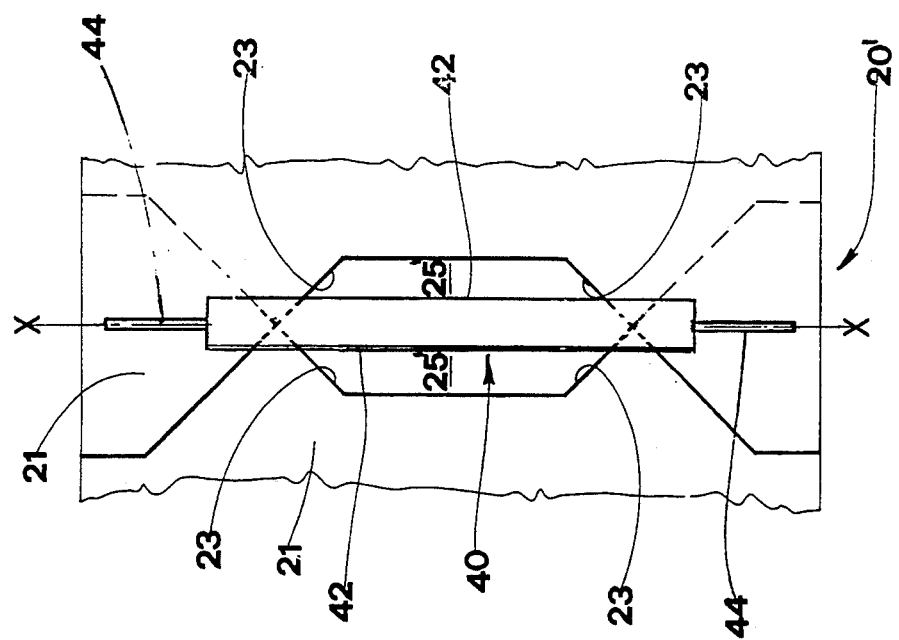

EQUIPMENT FOR THE CORRECTION OF ASTYGMATISM BY REMODELLING THE CORNEAL SURFACE BY MEANS OF PHOTO-ABLATION

BACKGROUND OF THE INVENTION

The invention relates to equipment for the correction of astygmatism by remodelling the corneal surface by means of photo-ablation.

The prior art teaches laser apparatus, known as excimer lasers, able to generate beams of radiation to vaporize, very exactly and regularly, very thin, microscopic layers (measurable in micrometers) of the eye corneal tissue. Such apparatus is used to remodel the external part of the cornea with the aim of eliminating various refraction defects.

The prior art teaches the use of masks and/or diaphragms which, correctly applied, allow the laser beam to reach and ablate the corneal surface in pre-established areas. By means of the use of such masks or diaphragms, whose aperture can be controlled and co-ordinated together with programmed laser-beam application times, it is thus possible to realise step-like sculptures in the cornea through a succession of photo-ablation removal operations of single uniform layers, of different-sized areas of the cornea itself.

SUMMARY OF THE INVENTION

The main aim of the present invention is to perfect equipment which, using excimer laser techniques, permits of effectively correcting astygmatism.

More in particular, the problem which the invention proposes to resolve is that of correcting corneal surface curvature defects, and the example is of the difference of curvature between the meridians passing through a point, a defect which is at the origin of ametropia or astygmatism.

The invention, as it is characterised in the claims that follow, solves the problem through the use, in combination with an excimer laser, of a mask structured to allow special modelling by photo-ablation, which modelling is differentiated according to the various meridians, of a part of the corneal surface arranged in front of the pupillar aperture.

Characteristic advantages of the invention are represented by its constructional and functional simplicity and by its intrinsic ability to adapt to various situations, thus making possible very fine regulation.

BRIEF DESCRIPTION OF THE DRAWINGS

Further advantages and characteristics of the present invention will better emerge from the detailed description that follows, made with reference to the accompanying drawings, which represent a preferred embodiment here illustrated in the form of a non-limiting example, and in which:

FIG. 3 shows, in enlarged scale, a particular of FIG. 2 in which the part of the corneal surface removed at the end of treatment is evidenced;

FIG. 4 shows, in enlarged scale, the part of the cornea removed at the end of treatment, from the section, according to line II—II of FIG. 1, perpendicular to the section performed according the line I—I;

FIG. 5 shows a schematic, partial perspective view;

FIGS. 6a, 6b and 6c show, in enlarged scale, four different embodiments of the particular of FIG. 1 relative to the conformation of the aperture (25) of the mask (20);

FIG. 8 shows a schematic frontal view of FIG. 7;

FIG. 9 shows, in enlarged scale, in the same frontal view as in FIG. 8, a further embodiment;

DESCRIPTION OF THE PREFERRED EMBODIMENTS

Figure 1:
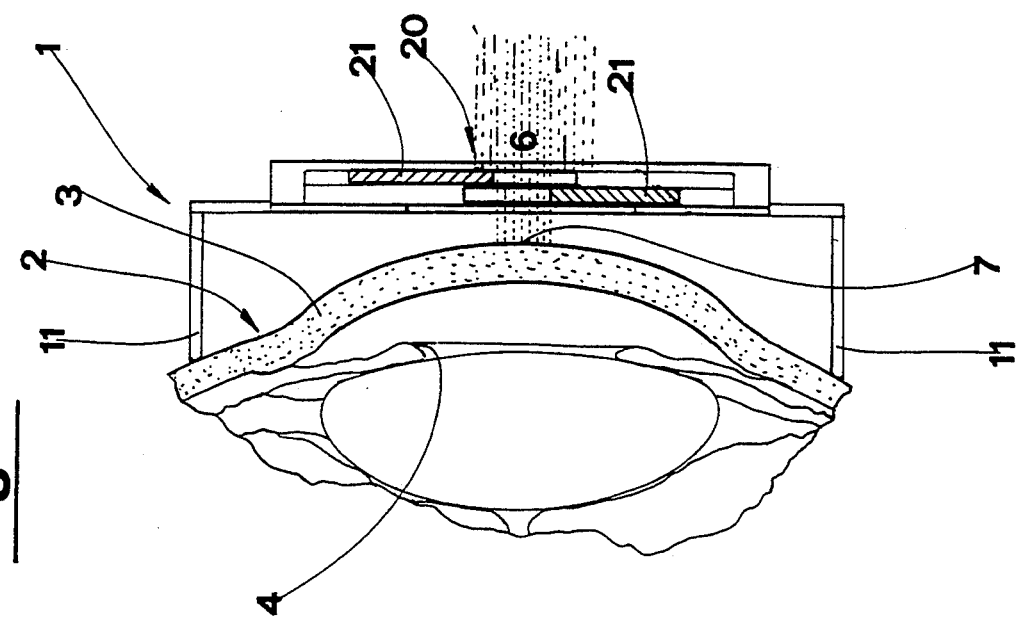
FIG. 1 shows a schematic frontal view of a first embodiment.
Figure 2:
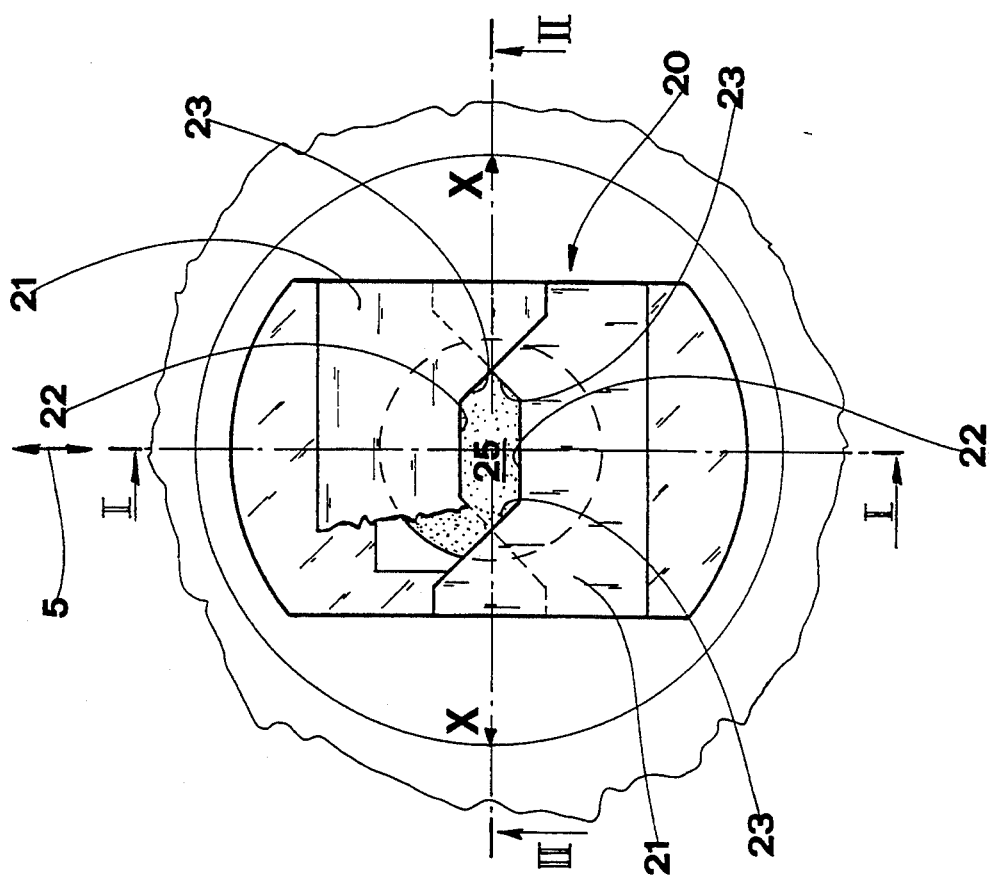
FIG. 2 shows a schematic section made according to line I—I of FIG. 1.

With reference to the FIGS., 1 denotes in its entirety a mask 1 applied to an eyeball 2 on a surface zone external to the cornea 3 situated in front of the pupillar aperture 4. The mask 1 comprises a structure or frame 11, cylindrical in shape and predisposed to rest directly on the eyeball 2. On the frame 11 is arranged an organ having the function of a diaphragm, denoted in its entirety by 20, which is essentially constituted by two identical flat plates 21 one alongside the other and sliding along the same direction, but in opposite senses, in relation to the frame 11. The two plates 21 are able to move independently of each other (thus allowing operations for the correction of irregular astygmatism to be performed) or they can be reciprocally constrained by means of a mechanism of the self-centering type, through which the contemporary symmetrical movement of the plates 21 with respect to the plate frame is produced, with reciprocal approaching or distancing movements which are symmetrical to a median reference plane X—X of the diaphragm 20 arranged perpendicularly to the plates 21 themselves. Each of the two plates 21 exhibits a recess which edge is constituted by a straight central part or side 22 to the extremities of which two connection parts or sides 23 are connected. In particular, in the illustrated embodiment, the said edge is constituted by a sort of broken line in which there is a straight principal side 22 and two contiguous connection sides 23. The straight principal side 22 is arranged perpendicularly to the relative sliding direction of the two plates 21, indicated by the arrows 5. The two connection sides 23 are also straight or slightly curved and describe, in the plane of the single plate 21, obtuse "internal" angles with the contiguous part or straight central side 22, with which they are connected. On the whole the two plates 21 are arranged one in front of the other so as to create a variable aperture 25 which, in a generic position, can be geometrically described as a polygon-shaped edge constituted by six sides; the two straight principal sides 22, which are opposite, reciprocally parallel and symmetrically facing each other, and the contiguous inclined side pairs 23. The variation of the aperture 25 of the diaphragm 20 is made by the reciprocally-distancing movement of the two plates 21 in the direction indicated by the arrows 5. These movements occur in relation to the said median plane of the mask 1, which is indicated by line X—X of FIG. 1, and which constitutes the median reference plane for the positioning of the mask itself with respect to the principal meridians or axes of the corneal surface zone involved in the treatment. The relative movement of the two plates 21 modifies the shape, hexagonal on the whole, which describes the variable aperture 25, simply by causing the approaching and the distancing of the two straight principal sides 22 with consequent "shortening or lengthening" of the contiguous connection sides 23. The length of the straight principal sides 22 is about 8 millimeters. The maximum distance obtainable between the two said straight principal sides 22, which corresponds to the maximum work aperture, is also about 8 millimeters. These dimensions are intended to be indicative, and substantially depend on the corneal surface area which must be involved in the treatment with reference to the diameter of the pupillar aperture. The mask is predisposed to be rested directly on the inferior part of its frame 11 on the eyeball 2 in such a way that the plates 21 are arranged parallel to a plane tangential to the corneal surface at the central point of the area to be treated.

The mask 1 is predisposed to direct, through its variable aperture 25, a laser beam 6 on to an area 7 of the corneal surface 3, situated in front of the pupillar aperture 4.

In order for the treatment of correction of myopic astygmatism to be performed, the mask 1 must be correctly oriented and positioned on the cornea 3. More precisely, the median reference plane of the mask 1, X—X, must be brought to coincide with the cornea 3 meridian plane external surface identifying the least curved meridian 31, that is the one characterised by the largest curvature degree. With such an orientation the two straight principal sides 22 of the mask 1 are perpendicularly located with respect to the meridian plane, and their intersection with the external surface of the cornea 3 identifies the most curved meridian 30, that is the meridian having the smallest degree of curvature, which in its turn is perpendicular to the above-mentioned least curved meridian 31. Once the above-described reference is established, the correction operation is proceeded to according to a succession of operative phases which first see the two plates 21 reciprocally positioned at the minimum (or maximum) reciprocal distance so as to identify the minimum (or maximum) pre-established value of the variable aperture 25 of the diaphragm 20. At the minimum value of the variable aperture 25 the external surface of the cornea 3 struck by the laser beam 6 is constituted by an extremely thin strip of a length which practically coincides with the length of the opposite straight principal sides 22. The influence of the contiguous connection sides 23 is negligible. Following this, a progressive reciprocal distancing of the two plates 21 is performed, according to a pre-established sequence of very small and predetermined relative movements according to the direction of the arrows 5, up until the maximum envisaged value of the variable aperture 25 is reached. According to and in synchrony with the subsequent and pre-established values imposed on the variable aperture 25, the laser beam 6, produced by an excimer laser, is brought to act. At each aperture value, the laser beam strikes a predetermined surface of the cornea 3 which internally comprises all the surface (only a part in cases where the initial conformation of the diaphragm 20 is at its maximum) identified by the aperture value immediately preceding and thus already struck by the previous application of the laser beam. Thus a modelling comprising tiny steps is obtained of the corneal zone struck by the successive single applications of the laser beam. At each application, as is well-known, a very thin layer of predetermined and uniform thickness is removed from the surface illuminated by the laser beam. When the operation is over, in the example herein provided, when the variable aperture 25 has reached its maximum value, the curvature of the interested zone is completely remodelled; indeed, at the meridian which was initially most curved 30, a sickle-shaped thickness of corneal tissue has been removed, evidenced in FIG. 3. Instead, at the meridian initially least curved, the total thickness removed is constant over all of the central area 7 equal in length to the straight principal sides 22. Starting from the ends of the area 7, however, the thickness removed diminishes progressively and gradually, so as to identify two zones 8 having a connecting function with the least curved meridian 31 of the non-treated part. The size and the gradualness of the connection depend on the angle comprised between each side 23 and the straight principal sides 22 contiguous to it.

The final result of the treatment consists in a remodelling of the corneal surface which does not modify the initial curvature of the least curved meridian while modifying, by diminishing it, the curvature of the most curved meridian. By correlating the values of the single apertures to be effected at each excimer laser beam 6 application with the thickness removed at each application, it is possible to generate on the plane of the most curved meridian (FIG. 3) a profile of any shape and in particular a profile having a constant curvature in the treated zone and equal to the curvature in the same zone for the least curved meridian (FIG. 4).

In this way, in the treated zone a spherical crown-shaped portion of surface is generated. In intermediate meridians, owing to the effect of the straightness and the reciprocal parallelism of the straight principal sides 22, intermediate corrections are obtained with respect to the corrections of the said two principal meridians.

For the correction of hypermetropic astygmatism, that is in order to modify the initial curvature of the least curved meridian so as to increase it, at least in a restricted zone corresponding to the pupillar aperture, with the aim of making it equal to that of the most curved meridian, the mask 1 can be equipped with an organ having the function of a diaphragm 20', which diaphragm 20' aperture is variable and geometrically identified by two semiapertures 25' and described by a closed edge in which a side 42 can be identified, apart from the straight principal sides 22 of a plate 21, which side 42 is opposite to the straight principal sides 22 and located closer to it with respect to the said X—X median plane. Each side 42 can be subjected to approaching and distancing movements from the relative opposite straight principal side 22.

Figure 7:
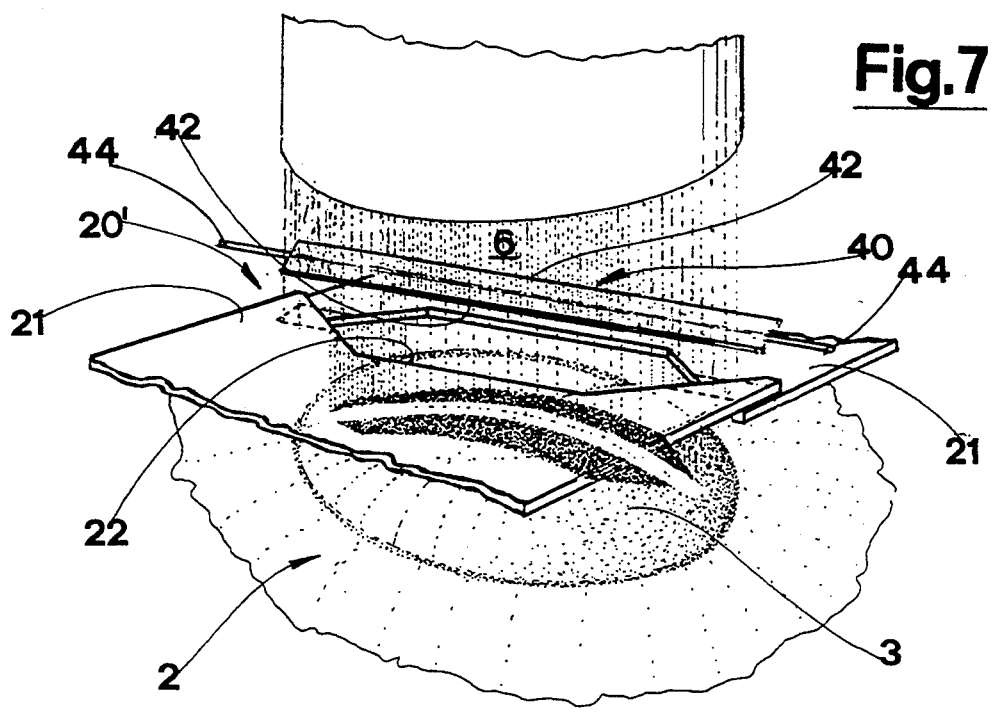
FIG. 7 shows a schematic perspective view of a further embodiment aimed at the correction of hypermetropic astygmatism.

As can clearly be deduced from FIGS. 7, 8 and 9, the two straight and parallel sides 42 of the two semiapertures 25' are identified by the edges of a thin plate 40, as they represent the two opposite and parallel sides of it.

The plate 40 is pivoted by means of two coaxial pivots 44 about an axis contained in the X—X plane and it is substantially parallel to the straight principal sides 22 of the plates 21. The length of the plate 40, which two sides 42 are located on opposite sides with respect to the axis of the coaxial pivots 44, is predisposed in such a way as to guarantee that the projection of te said sides 42 on one same plane (perpendiular to the direction of the laser beam), in reality coinciding with the plane containing the straight principal sides 22, is about the same as or at least not inferior to the corresponding projection on the same plane as the straight principal sides 22.

In the embodiment shown in FIG. 9, at both its opposite ends, the plate 40 is equipped with sides having a connection function 43 destined to constitute, together with the sides having the function of connection 23, the remaining sides of the closed edges of the two semiapertures 25'.

According to the angular position of the plate 40 about the relative coaxial pivots 44 with respect to the direction of the excimer laser beam 6 a strip of shadow is determined, of pre-established breadth according to the most curved meridian on which the X—X plane of the mask 1 is brought to coincide. The strip of shadow, which breadth is variable through the rotation of the plate 40, is thus aligned on the most curved meridian and is thus orthogonal to the least curved meridian which must be treated.

Figure 10:
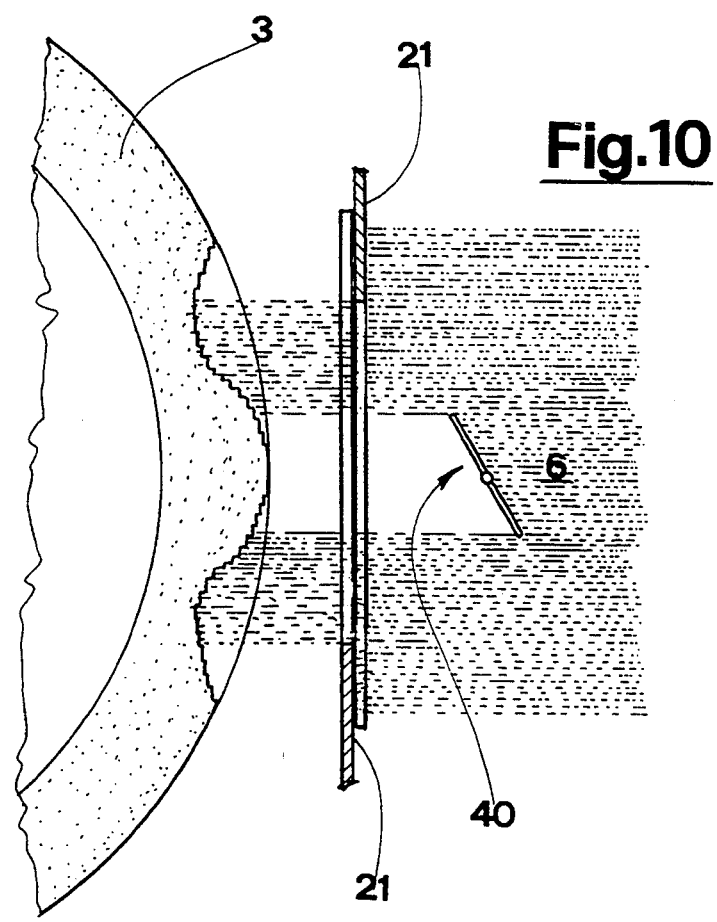
FIG. 10 shows, in enlarged scale and schematically, the result of a remodelling operation for the correction of hypermetropic astygmatism, according to a section made along the most curved meridian plane perpendicular to the line X—X.

By correlating the reciprocal distance values of the straight principal sides 22 with the inclination values of the plate 40 with respect to the direction of the incident excimer laser beam, at each application of the laser beam it is possible to generate any profile on the plane of the least curved meridian, and in particular a profile tract having, as can be seen in FIG. 10, a greater curvature than the initial curvature and equal to the curvature to be found in the same zone for the meridian which was initially most curved.

The presence of connection sides 43 on the plate 40 can be envisaged, with the function of performing a gradual connection of the zones placed at the extremity of the part to be treated. Normally, however, the plate 40 is not equipped with connection sides 43, but exhibits a substantially rectangular shape in which the sides 42 must be of length which is at least equal to the size of the maximum aperture of the mask evaluated in the direction of plane X—X.

What is claimed:

1. An assembly for correcting astigmatism by remodelling the corneal surface of an eyeball by means of photoablation, comprising:
   a mask having means for exposing, at each impulse of application of a laser beam, a pre-established surface of the cornea, said mask comprising a frame and a diaphragm, said diaphragm having a variable aperture defined by at least two middle sides, said two middle sides being disposed substantially parallel and opposite to one another, said two middle sides being reciprocally moveable with respect to each other and a median reference plane of said diaphragm, said median reference plane being disposed between said two middle sides, said median reference plane being a reference for the correct positioning of said diaphragm with respect to said corneal surface principal meridians, said variable aperture being further defined by at least two pair of angled side members, each pair of angle side members being disposed at respective opposite ends of said at least two middle sides.

2. The assembly according to claim 1, wherein said variable aperture has a convex polygonal shape.

3. The assembly according to claim 1, wherein said angled sides are contiguous with said middle side, said angled sides are substantially straight such that an angle between each angled side and the middle side is greater than 90° and less than 180°.

4. The assembly according to claim 3, wherein said diaphragm comprises two flat sheets, one of said sheets being slideably moveable over the other sheet such that said sheets move in opposite directions with respect to said median reference plane, each of said two flat sheets having a recess which includes said middle side and said pair of angled sides, the direction of the relative sliding of said two flat sheets being perpendicular to said middle sides.

5. The assembly according to claim 1, wherein said variable aperture is divided into two semi-apertures disposed on opposite sides with respect to said median reference plane, each of said semi-apertures being defined by said middle side and by at least one corresponding straight side which is disposed opposite to said middle side, but on the same side of said median referenced plane and is located closer to said median reference plane than said middle side; each of said straight sides being reciprocally moveable with respect to said respective middle side.

6. The assembly according to claim 5, wherein each of said straight sides is an opposite edge of a sheet which is pivotable about an axis that is parallel to the two middle sides; the length of said sheet being substantially equal to or greater than the length of said respective middle side.

7. The assembly according to claim 6, wherein said straight sides are located on opposite sides with respect to said axis.

8. The assembly according to claim 7, wherein the length of said straight sides is such that the projection of said sides on the corneal surface is not less than or equal to the corresponding projection of said middle sides on the corneal surface.

9. An assembly for correcting astigmatism by remodelling the corneal surface of an eyeball by means of photoablation, comprising:
   a mask having means for exposing, at each impulse of application of a laser beam, a pre-established surface of the cornea, said mask comprising a frame and a diaphragm, said diaphragm having a variable aperture defined by at least two middle sides, said two middle sides being disposed substantially parallel and opposite to one another, said two middle sides being reciprocally moveable with respect to each other and a median reference plane of said diaphragm, said median reference plane being disposed between said two middle sides, said median reference plane being a reference for the correct positioning of said diaphragm with respect to said corneal surface principal meridians, said variable aperture is divided into two semi-apertures disposed on opposite sides with respect to said median reference plane, each of said semi-apertures being defined by said middle side and by at least one corresponding straight side which is disposed opposite to said middle side, but on the same side of said median referenced plane and is located closer to said median reference plane than said middle side; each of said straight sides being reciprocally moveable with respect to said respective middle side.

10. The assembly according to claim 9, wherein each of said straight sides is an opposite edge of a sheet which is pivotable about an axis that is parallel to the two middle sides; the length of said sheet being substantially equal to or greater than the length of said respective middle side.

11. The assembly according to claim 10, wherein said straight sides are located on opposite sides with respect to said axis.

12. The assembly according to claim 11, wherein the length of said straight sides is such that the projection of said sides on the corneal surface is not less than or equal to the corresponding projection of said middle sides on the corneal surface.

* * * * *